United States Patent
Fujimoto et al.

(10) Patent No.: US 9,204,105 B2
(45) Date of Patent: Dec. 1, 2015

(54) IMAGING APPARATUS AND IMAGING METHOD

(71) Applicant: DAINIPPON SCREEN MFG. CO., LTD., Kyoto (JP)

(72) Inventors: Hiroki Fujimoto, Kyoto (JP); Masayoshi Kobayashi, Kyoto (JP); Takashi Miyake, Kyoto (JP); Sanzo Moriwaki, Kyoto (JP)

(73) Assignee: SCREEN HOldings Co., Ltd. (JP)

( * ) Notice: Subject to any disclaimer, the term of this patent is extended or adjusted under 35 U.S.C. 154(b) by 340 days.

(21) Appl. No.: 13/793,079

(22) Filed: Mar. 11, 2013

(65) Prior Publication Data
US 2013/0258076 A1 Oct. 3, 2013

(30) Foreign Application Priority Data

Mar. 30, 2012 (JP) ................................. 2012-078846
Jan. 25, 2013 (JP) ................................. 2013-011736

(51) Int. Cl.
*H04N 7/18* (2006.01)
*G01N 21/25* (2006.01)

(52) U.S. Cl.
CPC ............... *H04N 7/18* (2013.01); *G01N 21/253* (2013.01); *G01N 21/255* (2013.01); *G01N 2201/067* (2013.01); *G01N 2201/0631* (2013.01); *G01N 2201/0634* (2013.01)

(58) Field of Classification Search
None
See application file for complete search history.

(56) References Cited

U.S. PATENT DOCUMENTS

| | | | |
|---|---|---|---|
| 6,947,583 B2 | 9/2005 | Ellis et al. | 382/128 |
| 7,050,620 B2 | 5/2006 | Heckman | 382/133 |
| 7,120,282 B2 | 10/2006 | Langan | 382/128 |
| 7,129,473 B2 | 10/2006 | Ishihara et al. | 250/234 |
| 7,190,818 B2 | 3/2007 | Ellis et al. | 382/128 |
| 7,283,654 B2 | 10/2007 | McLain | 382/128 |
| 7,516,934 B2 | 4/2009 | Chu et al. | 248/550 |
| 7,718,131 B2 | 5/2010 | Jiang | 422/82.08 |
| 8,135,203 B2 | 3/2012 | Takagi et al. | 382/133 |
| 2006/0158754 A1* | 7/2006 | Tsukagoshi et al. | 359/851 |
| 2008/0149855 A1* | 6/2008 | Mehta et al. | 250/492.1 |
| 2008/0170463 A1* | 7/2008 | Murakami | 366/110 |

(Continued)

FOREIGN PATENT DOCUMENTS

| | | |
|---|---|---|
| JP | 06-148066 | 5/1994 |
| JP | 06-174635 | 6/1994 |
| JP | 11-037924 | 2/1999 |
| JP | 2001-083090 | 3/2001 |
| JP | 2003-524754 | 8/2003 |
| JP | 2008-064534 | 3/2008 |

(Continued)

OTHER PUBLICATIONS

Japanese Office Action dated Oct. 14, 2014 issued in corresponding Japanese patent Application No. 2013-011736 (2 pages).

*Primary Examiner* — Dave Czekaj
*Assistant Examiner* — Nam Pham
(74) *Attorney, Agent, or Firm* — Ostrolenk Faber LLP

(57) ABSTRACT

A preliminary image is obtained by irradiating illumination light, whose light quantity distribution is set at a standard state, to a specimen obtained by injecting fluid into a well from an illuminator capable of arbitrarily setting the light quantity distribution, for example, by a liquid crystal shutter, and a luminance distribution of the preliminary image is detected. As a result, luminance nonuniformity in the preliminary image is canceled by performing imaging with a light quantity distribution of illumination light to be incident on the well set such that an incident light amount is larger in a part with lower luminance.

14 Claims, 15 Drawing Sheets

(56) References Cited

U.S. PATENT DOCUMENTS

| | | | |
|---|---|---|---|
| 2009/0161943 A1* | 6/2009 | Yamashita et al. | 382/149 |
| 2010/0025567 A1 | 2/2010 | Lueerssen | 250/205 |
| 2010/0227316 A1* | 9/2010 | Suzuki et al. | 435/6 |
| 2011/0267493 A1* | 11/2011 | Kubo et al. | 348/223.1 |
| 2011/0293197 A1* | 12/2011 | Tsutsumi | 382/255 |

FOREIGN PATENT DOCUMENTS

| | | |
|---|---|---|
| JP | 2008-112190 | 5/2008 |
| JP | 2010-044004 | 2/2010 |
| JP | 2010-268723 | 12/2010 |
| WO | WO 99/60381 A1 | 11/1999 |
| WO | WO 02/37158 | 5/2002 |

\* cited by examiner

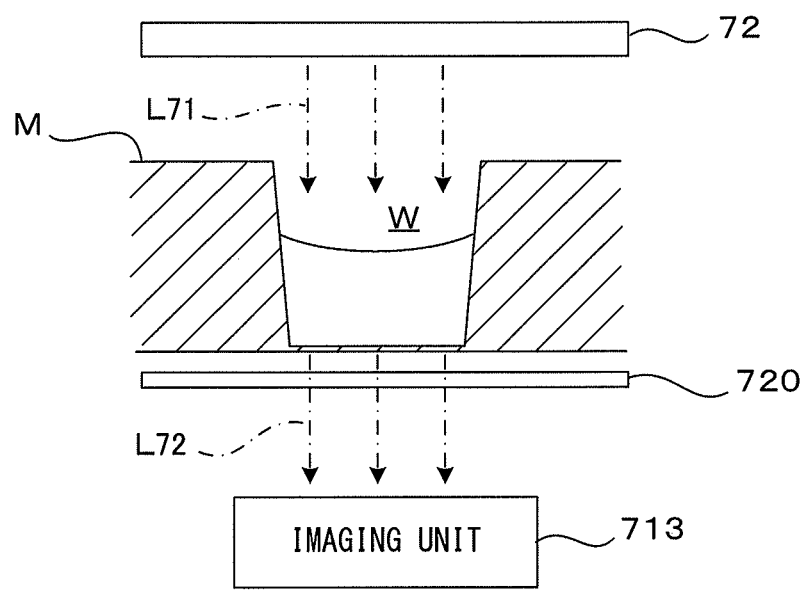
F I G. 1 5

IMAGING APPARATUS AND IMAGING METHOD

CROSS REFERENCE TO RELATED APPLICATION

The disclosure of Japanese Patent Applications enumerated below including specifications, drawings and claims is incorporated herein by reference in its entirety:
No. 2012-078846 filed on Mar. 30, 2012; and
No. 2013-011736 filed on Jan. 25, 2013.

BACKGROUND OF THE INVENTION

1. Field of the Invention

This invention relates to an imaging apparatus and an imaging method for imaging a specimen obtained by injecting fluid into a well and particularly to a technology for adjusting illumination light for illuminating the specimen in imaging.

2. Description of the Related Art

In medical or biological science experiments, cells or the like cultured in liquid or gel-like fluid injected into each well of a plate-like device in which a multitude of recesses called wells are arranged are, for example, observed and measured as a specimen. Such a device is, for example, called a microplate or a microtiter plate. In recent years, specimens are imaged by a CCD camera or the like and made into digital image data, and various image processings are applied to the image data for observation and analysis.

In this case, even if a light quantity distribution of illumination light irradiated to the specimen is made uniform, the quantity of light incident on the content (cells or the like) of the specimen may become nonuniform depending on the position due to light refraction caused by the meniscus of the surface (liquid surface) of the specimen and brightness non-uniformity resulting from this may be reflected on an image. As a conventional technology focusing on such a problem, in a technology disclosed in the specification of U.S. Pat. No. 7,718,131 for example, the density nonuniformity of an image resulting from the nonuniformity of illumination light is solved by reassembling an image of one well from partial images obtained by imaging in different incident directions of light a plurality of times.

In the conventional technology above, the incident direction of light is merely switched and light quantity shortage at a part where incident light is originally unlikely to reach, e.g. at a peripheral edge part of the recess is not solved. Thus, this has not gone far enough to make the quantity of light incident on the content of the specimen uniform. Such nonuniformity in the quantity of incident light causes luminance nonuniformity in an image of the content (cells or the like) of the specimen. For example, the luminance of an analysis object such as cells included in an image is used as important information at the time of automatic analysis such as the detection of cells and the discrimination of the type of the cells by image analysis. Nonuniformity in the incident light quantity reduces the accuracy of such an analysis and this problem cannot be dealt with in the above conventional technology.

SUMMARY OF THE INVENTION

This invention was developed in view of the above problem and aims to provide a technology capable of reducing the density nonuniformity of an image due to illumination light in a technology for imaging a specimen obtained by injecting fluid into a well.

An aspect of the present invention is an imaging apparatus comprising: a holder that holds a specimen holding plate substantially in a horizontal state, the specimen holding plate being formed with a well capable of holding liquid; a light illuminator that irradiates light from above the specimen holding plate held by the holder to a surface of a specimen obtained by injecting fluid into the well; a controller that controls a light quantity distribution of light to be incident on the surface of the specimen from the light illuminator based on a luminance distribution preliminarily measured at the well with the fluid; and an imager for obtaining an image of the specimen by imaging the specimen under light illumination at the light quantity distribution set by the controller.

Further, another aspect of the present invention is an imaging method for imaging a specimen obtained by injecting fluid into a well provided in a specimen holding plate, comprising: a preliminary imaging step of imaging the specimen and obtaining a preliminary image by irradiating light having a predetermined standard light quantity distribution toward a surface of the specimen from above the substantially horizontally held specimen holding plate; a detecting step of detecting a luminance distribution of the preliminary image; a setting step of setting a light quantity distribution of light to be incident on the specimen based on a detection result in the detecting step; and an image obtaining step of obtaining an image of the specimen under light illumination at the light quantity distribution set in the setting step.

In the invention thus configured, a light illumination condition in obtaining an image of the specimen is set based on the luminance distribution preliminarily measured using the well in which fluid is injected. By grasping the luminance distribution of the light to be incident on the specimen, the specimen can be imaged while the interior of the specimen is illuminated with light having a uniform light quantity distribution. Thus, according to the invention, it is possible to reduce luminance nonuniformity due to nonuniformity in the light quantity of illumination light and obtain a high-quality image preferably usable, for example, for image analysis.

Note that the unevenness of the surface of the specimen of this type may differ from specimen to specimen, for example, due to a variation in how to inject the fluid, wettability to a well wall surface and the like. According to the invention, such a variation of specimens can be dealt with since the light quantity distribution is set based on the luminance distribution preliminarily measured.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 15 is a diagram which shows an example of adjusting a light quantity distribution between a well and an imaging unit.

DETAILED DESCRIPTION OF THE PREFERRED EMBODIMENTS

Figure 1:
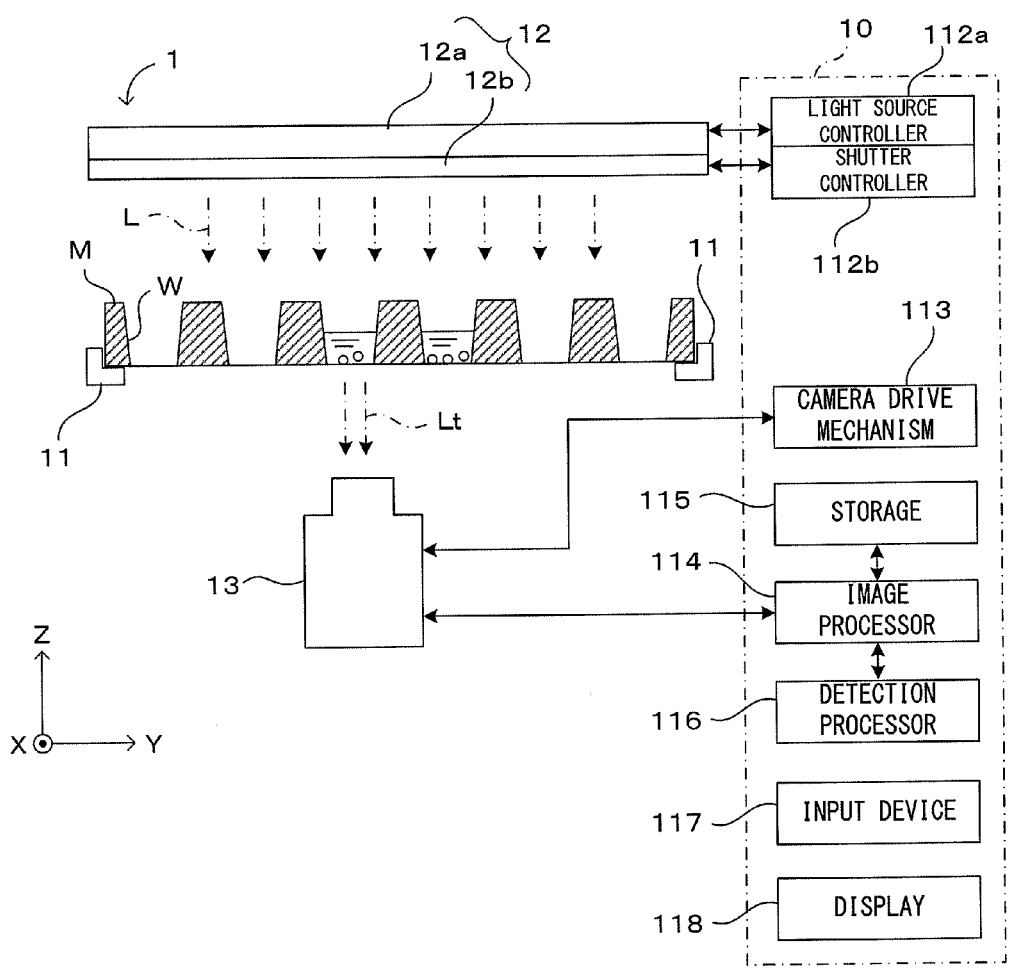
FIG. 1 is a diagram which shows a schematic configuration of a first embodiment of an imaging apparatus according to this invention.

FIG. 1 is a diagram which shows a schematic configuration of a first embodiment of an imaging apparatus according to this invention. This imaging apparatus 1 includes a holder 11 which holds a microplate M formed with a plurality of, e.g. 96 (12×8 matrix arrangement) wells W substantially in a horizontal state by coming into contact with a peripheral edge part of the lower surface of the microplate M, an illuminator 12 provided above the holder 11, an imaging unit 13 provided below the holder 11 and a controller 10 which performs a predetermined operation by governing these. Coordinate axes are set as shown in FIG. 1 for the following description. An X-Y plane is a horizontal plane and a Z-axis is a vertical axis.

The diameter and depth of each well W in the microplate M are typically about several millimeters. Fluid such as culture fluid, culture medium or reagent (only partly shown) is injected in each well W. Note that the number and size of the wells of the microplate as an object of this imaging apparatus 1 are not limited to these and arbitrary.

The illuminator 12 includes a light source 12a which is controlled by a light source controller 112a provided in the controller 10 and irradiates light toward the microplate M held by the holder 11 from above in response to a control command from the light source controller 112a. The light source 12a is a surface light source which has a planar size equal to or larger than that of the microplate M held by the holder 11 and emits light having a substantially uniform light quantity distribution from the lower surface thereof. Light emitted from the light source 12a is visible light and white light is particularly preferable. A fluorescent light source, an EL (Electroluminescence) light source, a light source in which a multitude of LED devices are arranged in a matrix or the like can be used as such a light source.

A transmission light quantity adjuster 12b formed of, e.g. a liquid crystal shutter is arranged on the lower surface of the light source 12a and controls a light quantity distribution of light emitted from the light source 12a toward the microplate M. More specifically, the transmission light quantity adjuster 12b increases and decreases the quantity of light transmission from one principle surface side toward the other principal surface side by opening and closing an optical path of light incident on the one principal surface side and transmitting to the other principal surface side for each tiny cell. The opening and closing of the shutter are controlled for each cell by a shutter controller 112b provided in the controller 10. In this way, as an area where the shutter is opened increases in a unit area for example, the quantity of light transmission increases in this region. By controlling the quantity of light transmission at each position in this way, the light quantity distribution of light incident on the microplate M can be finely controlled.

Note that an already commercialized liquid crystal display panel can be used as the illuminator 12 composed of the surface light source and the liquid crystal shutter as described above, for example. Specifically, a backlight provided in the liquid crystal display panel can be caused to function as the light source 12a and a liquid crystal unit including a driver circuit can be caused to function as the transmission light quantity adjuster 12b. Transmission light quantity distributions of various patterns can be realized in a similar manner to display figure patterns on a display panel. Further, if a display panel capable of color display is used, transmission patterns can be independently set for respective RGB wavelength components. A degree of light scattering may be increased by appropriately combining a diffuser with the display panel. Further, the surface light source may be not only of a shutter type such as liquid crystal, but also of a surface emission type such as an organic EL panel.

Light L whose light quantity distribution is controlled is emitted as illumination light to a plurality of wells W formed in the microplate M at once from the illuminator 12 configured as described above. Note that a configuration enabling the illuminator 12 to be retracted from a position above the holder 11 is desirable to facilitate the placement of the microplate M on the holder 11 and the removal of the microplate M from the holder 11. To this end, the illuminator 12 is desirably supported by a movable member such as a movable arm or a hinge (not shown).

The imaging unit 13 functions as a camera for imaging an image of the microplate M by receiving transmission light Lt emitted from the illuminator 12 and transmitting through the microplate M held by the holder 11 to a lower side. An imaging resolution is set at about 2400 dpi (dots per inch), for example. The imaging unit 13 is connected to a camera drive mechanism 113 provided in the controller 10, and the camera drive mechanism 113 causes the imaging unit 13 to move to scan in a horizontal plane along the lower surface of the microplate M held by the holder 11. Specifically, the imaging unit 13 can move and scan along the lower surface of the microplate M in this embodiment.

Image data obtained by the imaging unit 13 is fed to an image processor 114. The image processor 114 appropriately applies image processings to the image data from the imaging unit 13 and performs a predetermined arithmetic processing based on the image data. Data before and after the processings are stored and saved in a storage 115 if necessary. A detection processor 116 detects a characteristic part included in an image by performing a predetermined detection processing based on the image data fed from the image processor 114. This detection processing is a processing for detecting a region whose optical characteristic differs from its surrounding region in an image, for example, by analyzing luminance data of the image. Further, by calculating feature quantities for this region, classification as to the origin and type of this region can be made. Since various technologies are known for a processing for discriminating and detecting a part having a certain characteristic from an image in this way and feature quantities suitable for such a processing, they are not described in detail here.

A detection result by the detection processor 116 is also saved in the storage 115. Further, the image processor 114 performs an image processing based on the detection result by the detection processor 116 if necessary. The image data, to which appropriate image processings were applied, is fed, for example, to a display 118 including a display means such as a liquid crystal display, and the display 118 displays an image corresponding to the received image data and presents it to a user. Further, this imaging apparatus 1 includes an input device 117 for receiving the input of an operation instruction on the content of image processings and a display mode from the user. The input device 117 is, for example, an input receiving means such as a keyboard, a mouse or a touch pad or an appropriate combination of these, and a function desired by the user is realized by the controller 10 receiving the input of an instruction from the user and reflecting this on the operation of the apparatus.

This imaging apparatus 1 can be used in imaging an optical image of an imaging object such as fluid (in this specification, collective term for liquid, gel-like or semifluid solid and a substance injected into the well in a fluid state such as soft agar and then solidified) held in each well W and cells or the like included in the fluid and detecting a part having a predetermined optical characteristic, more specifically, a peculiar part having an optical property different from the fluid held in the well W from the optical image, using differences in the optical property. For example, the imaging apparatus 1 can be preferably used for the purpose of imaging cells or cell clumps (spheroids) in culture fluid or culture medium as an imaging object and automatically detecting such cells or the like by image processings.

Figure 2A:
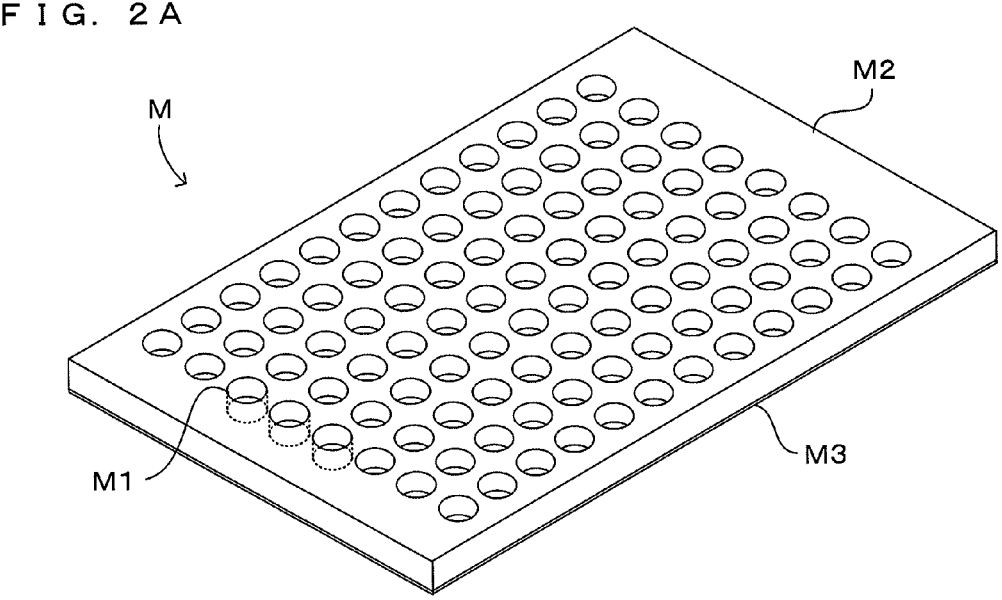
FIGS. 2A and 2B are views which show the structure of the microplate in more detail.
Figure 2B:
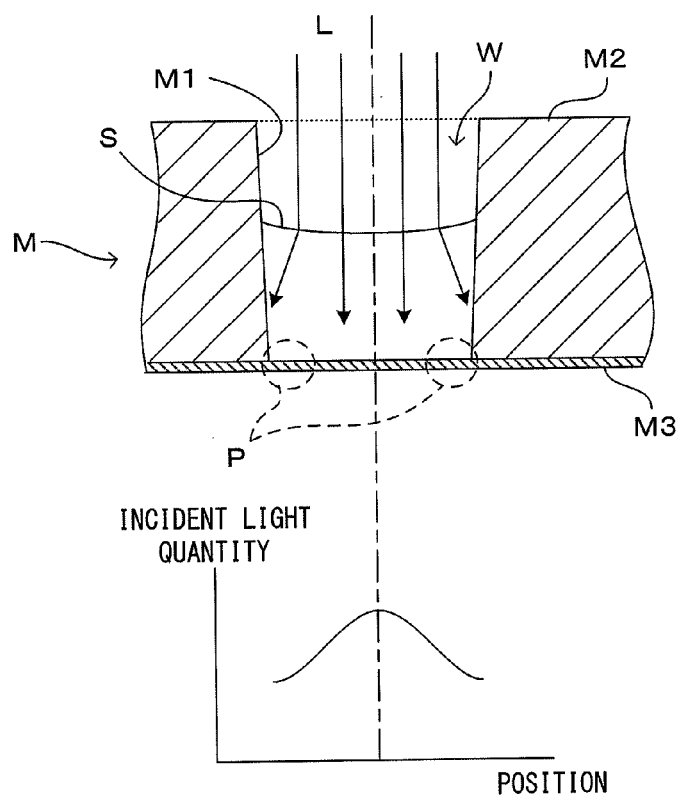

FIGS. 2A and 2B are views which show the structure of the microplate in more detail. As shown in FIG. 2A, the microplate M includes an upper plate M2 in which through holes M1 having a substantially cylindrical (more strictly, tapered to gradually reduce a cross-sectional area toward the bottom) side surface shape are regularly arranged at constant intervals in a two-dimensional matrix and a lower surface sheet M3 attached to the lower surface of the upper plate M2 to close the respective through holes M1.

The lower surface sheet M3 is closely fitted to the lower surface of the upper plate M2 and fluid can be held in spaces enclosed by the side surfaces of the through holes M1 of the upper plate M2 and the lower surface sheet M3. Specifically, these spaces function as the wells W for holding the fluid, the side surfaces of the through holes M1 serve as side wall surfaces of the wells M and the lower surface sheet M3 serves as the bottom surfaces of the wells W. The lower surface sheet M3 is a sheet body formed of transparent resin, e.g. PET (polyethylene terephthalate).

A case is thought where light is incident from above in a state where the fluid (e.g. liquid) is injected in the well W of the microplate M configured as described above. At this time, as shown in FIG. 2B, the surface (liquid surface) S of the injected fluid forms a meniscus. If light L having a uniform in-plane distribution is incident on the well W from above in this state, the incident light L propagates substantially straight to enter the fluid near the center of the well W where the liquid surface S is substantially horizontal. Contrary to this, a propagation direction of the light incident on the liquid surface near the side wall surface of the well W is bent due to refraction on the liquid surface. Due to this, illumination light is unlikely to reach a peripheral edge part P of the well bottom surface near the side wall surface and the quantity of incident light tends to become smaller as compared with the vicinity of the center.

Such a distribution of the incident light quantity means that the quantity of illumination light incident, for example, on an object such as cells cultivated on the bottom of the well differs depending on the position. Thus, in an image of the same object, luminance differs depending on the position in the well W. This could cause an error in a process of analyzing an object using the luminance of the imaged object as significant information.

Accordingly, in this embodiment, the illuminator 12 is provided which can control the illumination light quantity distribution as described above. In an imaging operation to be described later, the light quantity distribution of the illumination light at the time of imaging is so set that uniform light is incident on the well bottom based on a luminance distribution in a preliminary image obtained in advance by imaging a specimen as an imaging object and imaging is performed under this illumination condition.

Note that a surface state of the fluid injected into the well W differs from specimen to specimen due to the viscosity of the fluid, wettability to the well wall surface, operation variation at the time of injection and the like. Due to this, the distribution of the illumination light quantity on the well bottom could differ from specimen to specimen. A technical concept of this embodiment can deal with a state of the liquid surface which differs from specimen to specimen as just described. Here, it is assumed that the liquid surface forms a downwardly convex meniscus as shown in FIG. 2B to facilitate understanding.

Figure 3A:
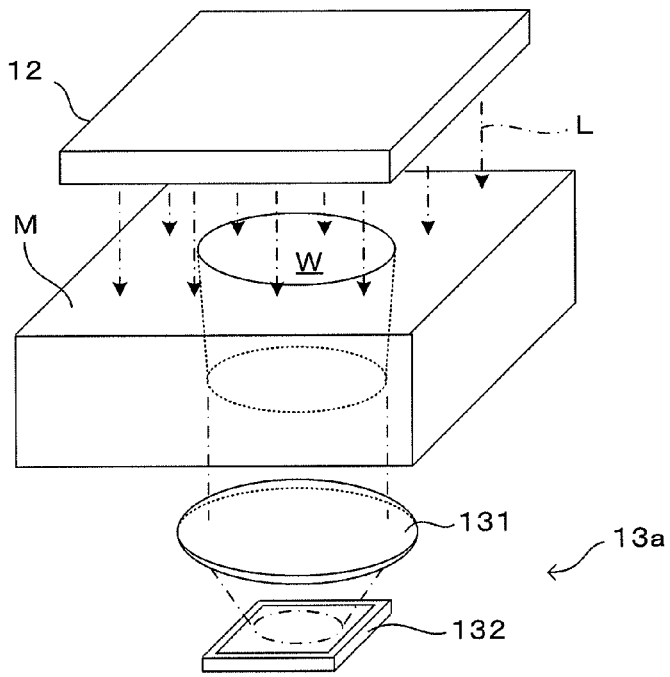
FIGS. 3A and 3B are views which show two imaging modes which can be adopted by the apparatus of this embodiment.
Figure 3B:
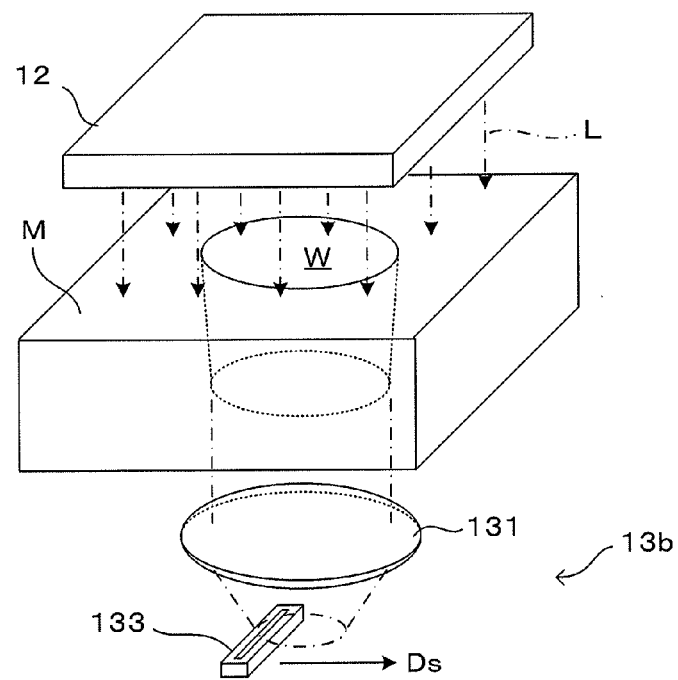

FIGS. 3A and 3B are views which show two imaging modes which can be adopted by the apparatus of this embodiment. Although an example in which one well W is imaged is cited here, the same way of thinking applies also in the case of imaging a plurality wells at once. In a first mode shown in FIG. 3A, substantially uniform illumination light L from the illuminator 12 is incident on the well W as an imaging object from above. An imaging optical system 131 and a two-dimensional imaging device 132 in which a multitude of minute light receiving elements are two-dimensionally arranged are successively arranged below the well W. These configure the imaging unit 13 and, in FIG. 3A, are denoted by 13a to distinguish the imaging unit having this configuration from others. A CCD sensor, a CMOS sensor or the like can be used as the two-dimensional imaging device 132. Note that although the imaging optical system 131 is shown as a single lens here, it may be composed of a plurality of lenses.

Transmission light from the bottom surface of the well W is converged by the imaging optical system 131 on a light receiving surface of the two-dimensional imaging device 132 arranged below the imaging optical system 131. This causes an image of an object (cells or the like) distributed on the well bottom and its vicinity to be imaged on the light receiving surface of the two-dimensional imaging device 132, and an image of the well is obtained by the two-dimensional imaging device 132. This mode can be said to be a combination of an illuminator of a two-dimensional pattern and an imaging device of a two-dimensional pattern.

On the other hand, in an imaging unit 13b of a second mode shown in FIG. 3B, a linear imaging device (line sensor 133) in which a multitude of minute light receiving elements are linearly arranged is arranged below an imaging optical system 131. The linear imaging device 133 performs imaging while being moved to scan in a direction Ds perpendicular to a longitudinal direction (light receiving element arrangement direction) of the linear imaging device 133, whereby a two-dimensional image of the well W is obtained as in the first mode. This mode is a combination of an illuminator of a two-dimensional pattern and an imaging device of a one-dimensional pattern. Regardless of which of the configurations of the above modes the imaging unit 13 has, an imaging operation described below can be applied and functions and effects obtained thereby are basically same.

Figure 4:
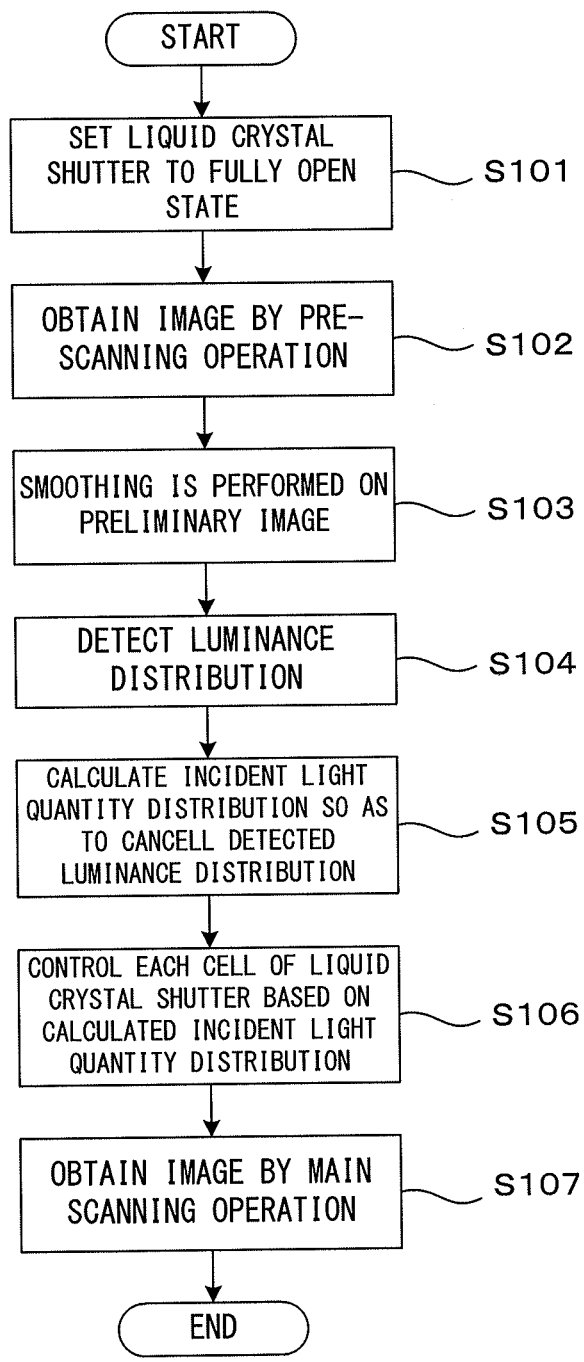
FIG. 4 is a flow chart which shows an imaging operation in the first embodiment.

FIG. 4 is a flow chart which shows an imaging operation in the first embodiment. Images of the wells W including the specimens are obtained by the controller 10 controlling the respective components of the apparatus to perform the operation of FIG. 4 after the microplate M holding the specimens in the wells W is set on the holder 11 by an operator. First, the liquid crystal shutter of the transmission light quantity adjuster 12*b* is set in a fully open state, i.e. a state is set where light from the light source 12 is transmitted at all in-plane positions (Step S101). In this way, substantially uniform light emitted from the light source 12*a* is directly incident on the surfaces of the specimens held in the wells W. Light quantity distributions at this time are set as standard states which are bases of an operation to be performed later.

In this state, the imaging operation (pre-scanning operation) by the imaging unit 13 is performed (Step S102). An image obtained at this time is called a "preliminary image" in this specification. The preliminary image has luminance non-uniformity due to the refraction of the illumination light on the specimen surfaces and is not necessarily suitable for various analyses as it is. In this embodiment, the preliminary image is used as a sample for optimizing an illumination condition in the main scanning operation to be performed later.

Subsequently, image smoothing is performed on the preliminary image (Step S103). Specifically, relatively high spatial frequency components included in the image are removed by appropriate filtering or the like. Although images of the cells or the like in the specimens are included in the preliminary image, what is necessary at this point of time is information on a luminance distribution due to the illumination light and information on the cells or the like is not necessary. A background image is obtained by removing images of the cells or the like from the image through smoothing corresponding to the assumed size of the cells or the like.

By obtaining luminance in the thus obtained background image pixel by pixel, a luminance distribution in this image is detected (Step S104). The luminance distribution detected here shows the distribution of the incident light quantity on the well bottom surface. Subsequently, such a distribution of the illumination light quantity as to cancel the thus detected luminance distribution is calculated so that a uniform incident light quantity distribution is obtained in actual imaging (Step S105).

Figure 5A:
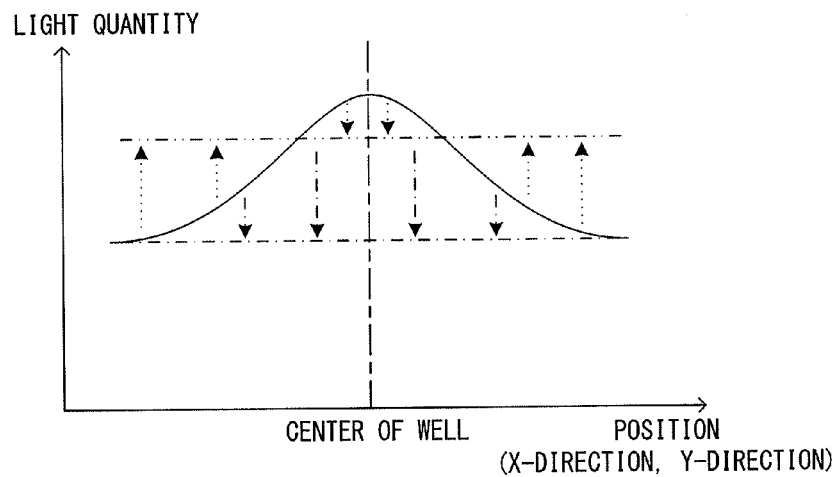
FIGS. 5A and 5B are diagrams which show a calculation model of the illumination light quantity distribution.
Figure 5B:
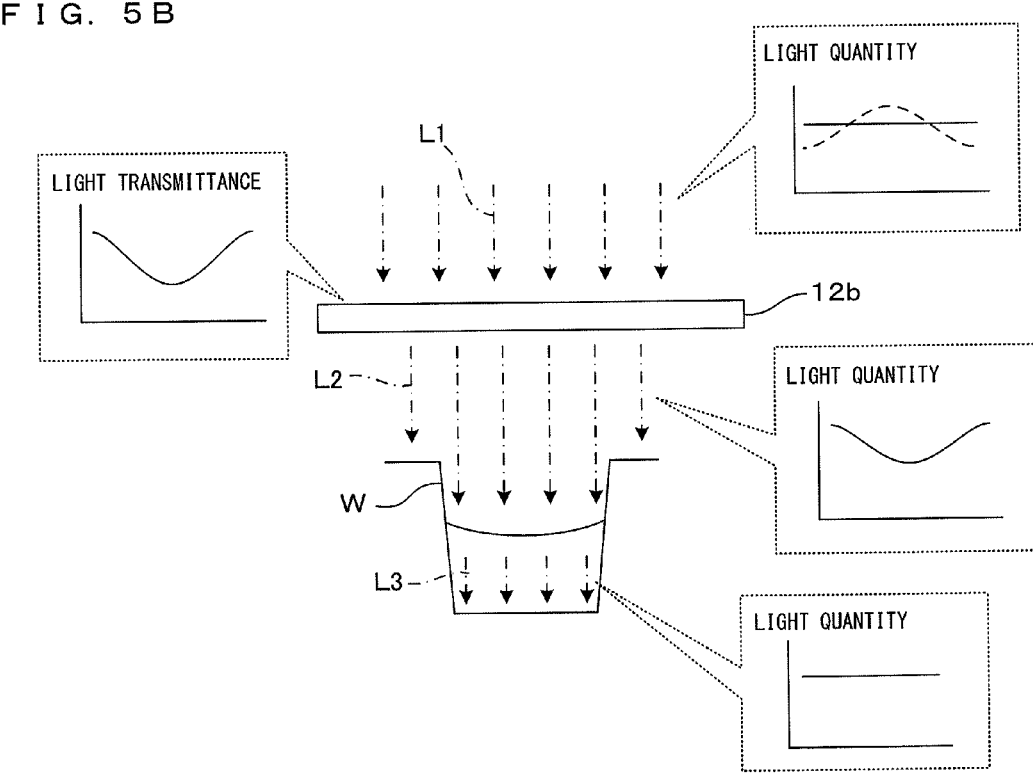

FIGS. 5A and 5B are diagrams which show a calculation model of the illumination light quantity distribution. When the specimen surface has a downwardly convex meniscus as shown in FIG. 2B, it is assumed that a luminance distribution in which luminance is high in a central part of the well and low in a peripheral edge part is obtained. This is a reflection of the incident light quantity on the well bottom surface. At this time, light itself emitted from the light source 12*a* is substantially uniform in a plane. Thus, if the incident light quantity on the specimen surface corresponding to a high luminance part is suppressed to a low level in advance as shown by dashed-dotted line in FIG. 5A, the light quantity distribution on the well bottom surface can be approximated to a more uniform state. Such an adjustment of the light quantity distribution can be realized by controlling a transmission pattern in the transmission light quantity adjuster 12*b*.

Even if the light itself emitted from the light source 12*a* has a certain light quantity distribution (shading), this can be canceled by adjusting the illumination light quantity distribution as described above. Similarly, luminance nonuniformity due to the unevenness of the specimen surface can also be canceled.

Note that although the light quantity distribution becomes more uniform according to the above principle, the overall light quantity is reduced and the image becomes darker. However, if uniform brightness can be ensured, it is not really acknowledged as a problem that the entire image becomes darker. Further, depending on the type of the cells, a state of the cells themselves may be changed by strong light stimulus. Accordingly, such an adjustment method of reducing the incident light quantity in a bright part is thought to be practically sufficient. On the other hand, for an application requiring more brightness, a measure for increasing the quantity of light emitted from the light source 12*a* may be taken if necessary as shown by dotted line in FIG. 5A.

FIG. 5B diagrammatically shows a light quantity distribution at each position on an optical path of illumination light. The light quantity of light L1 emitted from the light source 12*a* is uniform (solid line) or has a certain distribution (broken line) as shown in an upper right balloon box. On the other hand, light transmittance in the transmission light quantity adjuster 12*b* set from the preliminary image has a distribution which is an inverse of the luminance distribution in the preliminary image as shown in an upper left balloon box.

As a result, in the light quantity distribution of light L2 having transmitted through the transmission light quantity adjuster 12*b*, the light quantity becomes larger in a region with lower luminance in the preliminary image as shown in a middle right balloon box. If such light L2 is incident on the specimen in the well W, the light quantity of light L3 incident on the well bottom surface is substantially uniform independently of the position as shown in a lower right balloon box.

The light quantity distribution of the light incident on the well bottom can be properly set by controlling the transmission light quantity adjuster 12*b* based on the luminance distribution in the preliminary image to adjust the light quantity distribution of the illumination light to be incident on the well W. Specifically, it is only necessary to calculate the light quantity distribution on the specimen surface which makes the light quantity distribution uniform on the well bottom surface and obtain a transmission pattern of the transmission light quantity adjuster 12*b* to realize that.

Referring back to FIG. 4, the imaging operation is further described. By controlling each cell of the liquid crystal shutter of the transmission light quantity adjuster 12*b* based on the above principle, the light quantity distribution of the light to be incident on the well bottom surface can be uniformized (Step S106). By performing imaging (main scanning operation) by the imaging unit 13 in this state, an image of the well W including the object such as cells can be obtained (Step S107).

In the thus configured imaging operation, by performing imaging in a state where the object distributed on the well bottom is illuminated by substantially uniform light, it is possible to obtain an image free from luminance nonuniformity due to the refraction of the illumination light on the specimen surface. By making the thus obtained image an output image for various analyses, it is possible to provide a user with a high-quality image with little luminance nonuniformity due to illumination light in this embodiment.

Note that it is desirable to set the illumination light quantity distribution for each well in imaging a plurality of wells W. In this case, one well may be selected, a series of processings shown in FIG. 4 may be performed and, after completing them, another well as an object may be selected anew and the above processings may be repeated. Alternatively, a plurality of wells may be placed within an imaging field of view, one pre-scanning operation may be performed for all these wells, and the main scanning operation may be performed after a luminance distribution of a background image is obtained for each well and an illumination light quantity distribution is set.

Next, a second embodiment of the imaging apparatus according to this invention is described. In the imaging apparatus 1 of the above first embodiment, the illuminator 12 arranged above the microplate M includes the surface light source 12a having a substantially uniform light quantity distribution. Contrary to this, the imaging apparatus of the second embodiment described next includes a line light source formed by arranging light emitting elements in a row, and illumination light is caused to be incident on all the wells W by moving this and scanning relative to the wells W. Since the apparatus configuration and basic operations of the respective components are the same as in the first embodiment except for this point, the same configurations are denoted by the same reference signs and not described below.

Figure 6A:
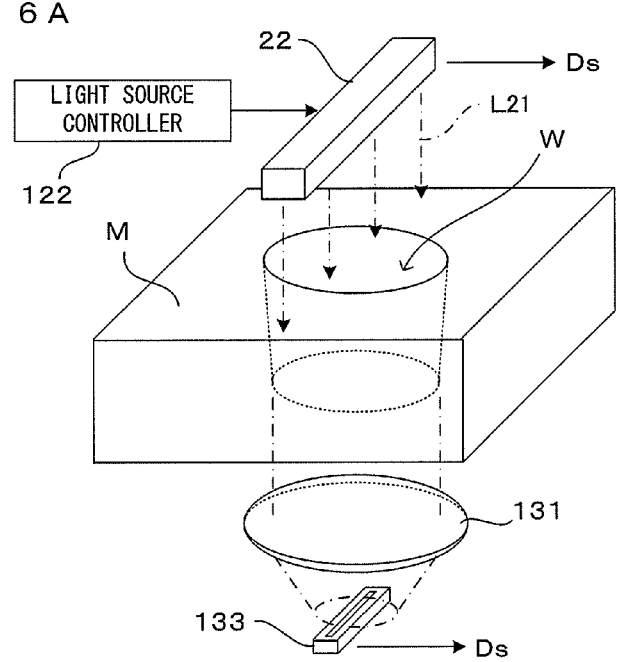
FIGS. 6A to 6C are views which show a main part of the second embodiment of the imaging apparatus according to this invention.
Figure 6B:
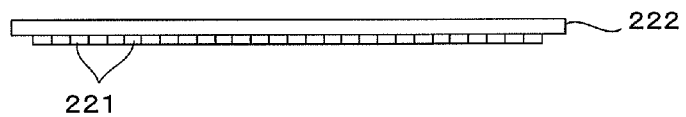
Figure 6C:
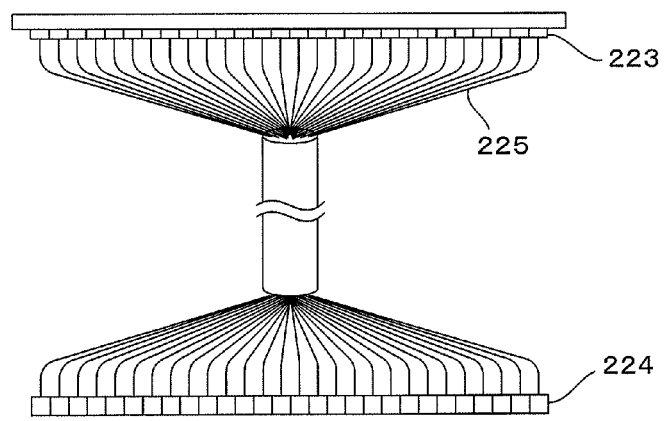

FIGS. 6A to 6C are views which show a main part of the second embodiment of the imaging apparatus according to this invention. As shown in FIG. 6A, a bar-like illuminator 22 for emitting light L21 toward the upper surface of the microplate M is provided above a microplate M held by a holder 11. Further, an imaging unit 13 includes the linear imaging device 133 shown in FIG. 3B and a longitudinal direction of the illuminator 22 is parallel to an arrangement direction of the light receiving elements in the linear imaging device 133. That is, this mode is a combination of an illuminator of one-dimensional pattern and an imaging device of one-dimensional pattern.

The illuminator 22 is moved to scan in a direction Ds relative to the microplate M integrally with the linear imaging device 133 in synchronization with a scanning movement of the linear imaging device 133 relative to the microplate M. Specifically, in this embodiment, a two-dimensional image is obtained by changing the position of the linear imaging device 133 relative to the well W every second while imaging a part of the well W facing the linear imaging device 133. At this time, the illumination light from the illuminator 22 is irradiated to the part imaged by the linear imaging device 133 in a concentrated manner every second.

An illuminator in which a multitude of minute light emitting elements (e.g. LEDs) 221 are arranged in a longitudinal direction of a bar-like base member 222 as shown in FIG. 6B, e.g. an LED array or a bar LED can be used as the illuminator 22. Each light emitting element 221 is individually controlled by a light source controller 122. In other words, the light source controller 122 can individually control an on timing and a light emission quantity of each light emitting element 221.

Note that each of the multitude of light emitting elements 221 provided in the illuminator 22 needs not be completely independently controlled. Specifically, several adjacent light emitting elements may be formed into one group and an on/off control may be performed by the group. Further, on and off states or the light emission quantity can be adjusted as a mode of the control. On and off timings, an applied voltage and an on-duty in intermittent lighting and the like can be used as a control object.

In the thus configured illuminator 22, a light quantity distribution in the arrangement direction of the light emitting elements 221 can be arbitrarily set by individually controlling each of the light emitting elements 221 arranged in a row. Further, a light quantity distribution in the scan moving direction Ds perpendicular to the arrangement direction of the light emitting elements 221 can be arbitrarily changed by changing the emitting state of each light emitting element 221 in synchronization with the scanning movement of the illuminator 22. A two-dimensional distribution of the quantity of light (more strictly, an integration value thereof) to be incident on the well W can be arbitrarily set also in this embodiment by a combination of a temporal change of the light emission quantity in one light emitting element 221 and differences in the light emission quantity among the plurality of light emitting elements 221.

As shown in FIG. 6C, the illuminator 22 may include a multitude of light emitting elements 223, a multitude of light projecting members 224 and a light guide member 225. Each light emitting element 223 is individually controlled. The light projecting members 224 are arranged above the microplate M and arranged in a row in the same direction as the arrangement direction of the light emitting elements of the linear imaging device 133 and emit light toward the upper surface of the microplate M. The light guide member 225 is composed of, for example, an optical fiber for optically connecting the multitude of light emitting elements 223 and the multitude of light projecting members 224 one on one. Functions and effects similar to the above ones can be obtained also by such a configuration.

Figure 7:
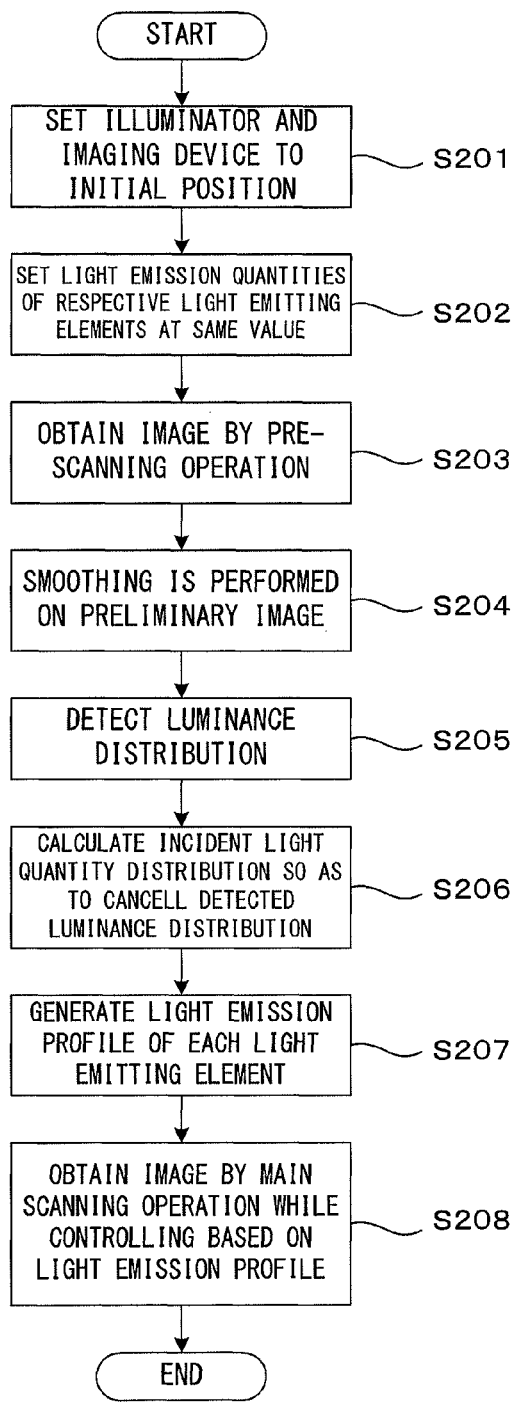
FIG. 7 is a flow chart which shows an imaging operation in the second embodiment.

FIG. 7 is a flow chart which shows an imaging operation in the second embodiment. In the imaging operation of this embodiment, the illuminator 22 and the linear imaging device 133 are first positioned at a predetermined initial position (one end of a region to be imaged) (Step S201). Then, the light emission quantities of the respective light emitting elements 221 are set at the same value to set a standard state (Step S202). Specifically, drive voltages applied to the respective light emitting elements 221 are set at the same value. Although the light emission quantity may vary in each light emitting element 221 even if the same voltage is applied, such differences are ignored since they can be canceled like the light quantity distribution of the light source 12a in the first embodiment.

Subsequently, as in the first embodiment, the acquirement of a preliminary image by a pre-scanning operation (Step S203), the smoothing of the preliminary image (S204), the detection of a luminance distribution of a background image after the smoothing (S205) and the calculation of an illumination light quantity distribution to cancel the luminance distribution (Step S206) are successively performed. Based on the thus obtained illumination light quantity distribution, a light emission profile for specifying the emitting state of the light emitting element 221 is set for each light emitting element 221 (or for each light emitting element group) (Step S207).

Figure 8:
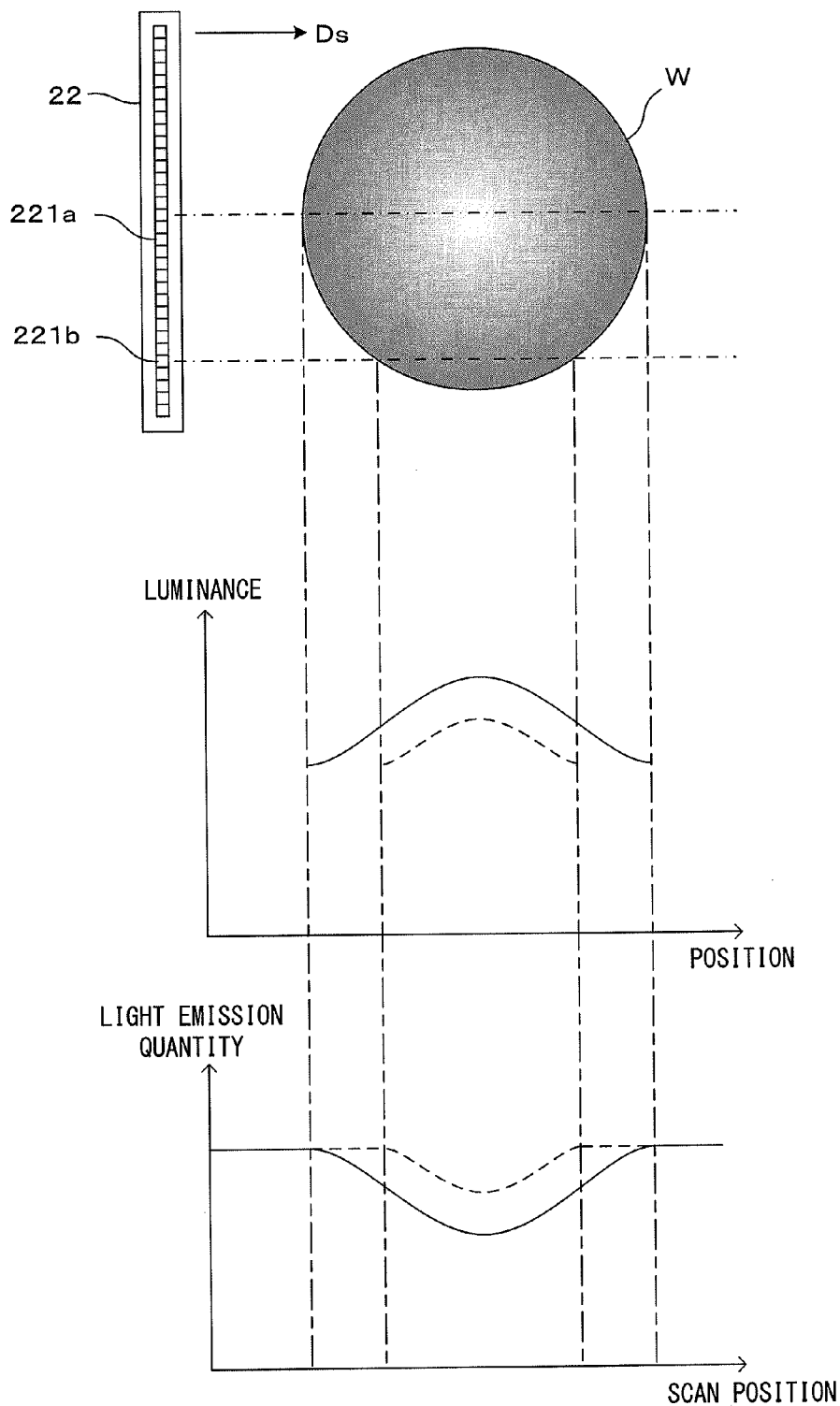
FIG. 8 is a diagram which shows an idea of the light emission profile.

FIG. 8 is a diagram which shows an idea of the light emission profile. As shown in an upper part of FIG. 8, the illuminator 22 is moved for scanning in the scan moving direction Ds to pass above the well W, whereby a preliminary image is imaged. An example of a luminance distribution obtained from the preliminary image is shown in a middle part of FIG. 8. Solid line represents a luminance distribution at a position right below a path of a light emitting element 221a passing above the vicinity of the center of the well W. Broken line represents a luminance distribution at a position right below a path of a light emitting element 221b passing above the vicinity of the peripheral edge of the well W.

A relationship (light emission profile) between the light emission quantity of each light emitting element and the position (scan position) of the light emitting element in the scan moving direction Ds in a main scanning operation necessary to cancel such a luminance distribution is shown in a lower part of FIG. 8. Solid line represents a light emission profile for the light emitting element 221*a* passing above the vicinity of the center of the well W. Broken line represents a light emission profile for the light emitting element 221*b* passing above the vicinity of the peripheral edge of the well W.

While a state where each light emitting element 221 is caused to emit a fixed quantity of light is set as a basic state, the light emission quantity of the corresponding light emitting element is reduced at a position where a luminance increase is seen in the preliminary image, with the result that the light quantity distribution of the illumination light to be incident on the well bottom surface can be made substantially uniform. In this way, the light emission profile based on the luminance distribution of the preliminary image can be generated for each light emitting element 221 (or for each light emitting element group) provided in the illuminator 22.

Referring back to FIG. 7, the imaging operation of this embodiment is further described. When the light emission profile of each light emitting element is generated in this way, an image of the well W is obtained by performing the main scanning operation by the linear imaging device 133 while controlling light emission from each light emitting element 221 based on this light emission profile to adjust the light emission quantity (Step S208). At this time, the light emission quantity of each light emitting element 221 is adjusted in real time in synchronization with the scanning movement of the linear imaging device 133, whereby imaging can be performed in a state where a fixed quantity of light is incident on the well bottom surface. Thus, similar to the first embodiment, it is possible to obtain an image free from luminance nonuniformity due to the refraction of the illumination light on the specimen surface.

Figure 9:
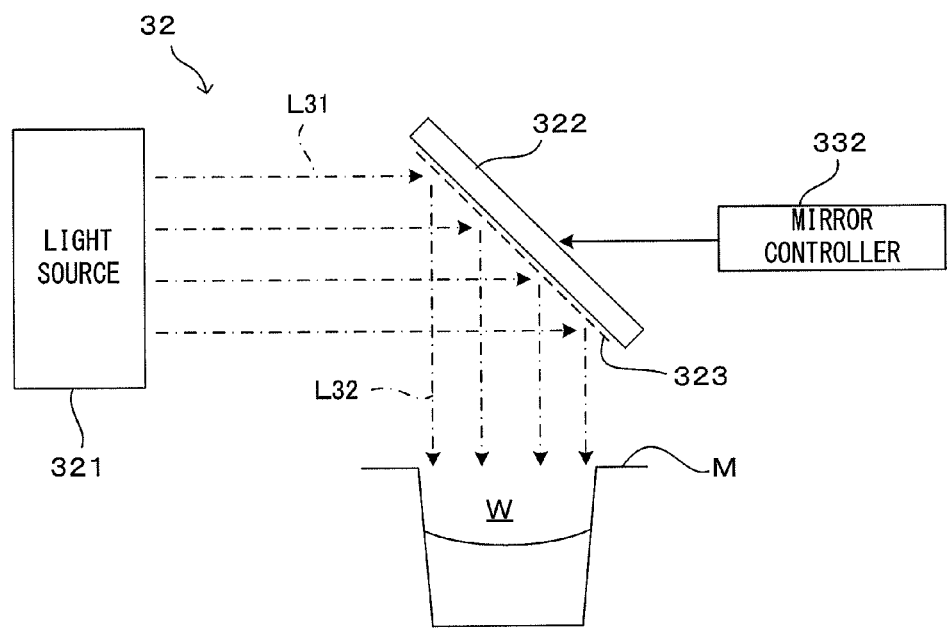
FIG. 9 is a diagram which shows a main part of a third embodiment of the imaging apparatus according to this invention.

FIG. 9 is a diagram which shows a main part of a third embodiment of the imaging apparatus according to this invention. This embodiment is characterized in the configuration of an illuminator 32 and the configuration of the first or second embodiment can be applied for other parts. Thus, a characteristic part of this embodiment is mainly described here.

The illuminator 32 of this embodiment includes a light source 321 which emits light and a reflecting mirror unit 322 which is arranged above a well W and reflects light L31 emitted from the light source 321 and causes it to be incident on the well W. The reflecting mirror unit 322 is such that a multitude of minute reflecting mirrors 323 capable of adjusting an angle independently of each other are arranged. The angle of each of a plurality of reflecting mirrors 323 is controlled by a mirror controller 332 provided in a controller 10. A DMD (Digital Mirror Device) used in a display device can be, for example, used as such a reflecting mirror unit 322. Further, the usable light source 321 and reflecting mirror unit 322 are either of a two-dimensional (surface light source) type as in the first embodiment or of a one-dimensional (line light source) type as in the second embodiment. In the case of the one-dimensional type, a scanning movement at least synchronized with a scanning movement of an imaging device of the reflecting mirror unit 322 is necessary as in the second embodiment.

In such a configuration, it is possible to control a light quantity distribution of light L32 to be incident on the well W and uniformize the incident light quantity on the well bottom by changing a reflection direction of light incident on the light source 321 at each position by the reflecting mirror unit 322.

Figure 10A:
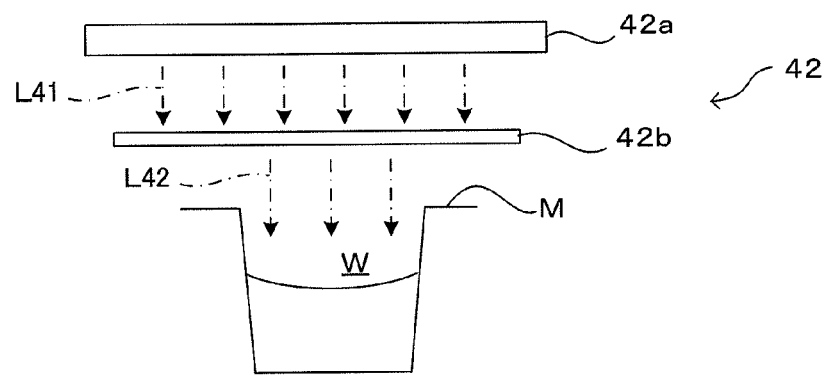
FIGS. 10A and 10B are views which show a main part of a fourth embodiment of the imaging apparatus according to this invention.
Figure 10B:
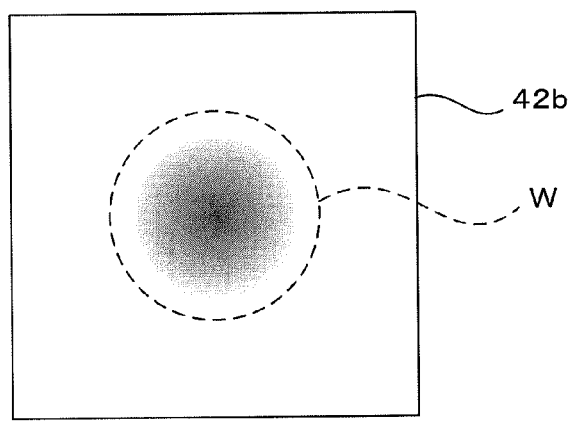

FIGS. 10A and 10B are views which show a main part of a fourth embodiment of the imaging apparatus according to this invention. In the above respective embodiments, the preliminary image is obtained by performing the pre-scanning operation prior to the main scanning operation and the illumination light quantity distribution is set from the luminance distribution of the preliminary image. Contrary to this, in the apparatus of the fourth embodiment, the pre-scanning operation in individual imaging is omitted by setting a light quantity distribution of illumination light in advance, assuming illumination light quantity nonuniformity due to refraction on a specimen surface. Such a mode is suitable, for example, when a variation of a surface state of a specimen is small such as when the viscosity of fluid to be injected into a well W is low and the injection of the fluid is automated.

As shown in FIG. 10A, a surface light source 42*a* having a substantially two-dimensionally uniform light quantity distribution is arranged above the well W in an illuminator 42 of this embodiment. A transmission light quantity adjusting member 42*b* formed with a shade pattern as shown in FIG. 10B is arranged between the surface light source 42*a* and the well W. The transmission light quantity adjusting member 42*b* is a sheet-like or plate-like member having optical transparency and the color becomes dark in a part corresponding to the center of the well W and becomes lighter with distance from the center as shown in FIG. 10B.

Thus, when the transmission light quantity adjusting member 42*b* is arranged above the well W, light L41 emitted from the surface light source 42*a* has a substantially uniform light quantity distribution, whereas light L42 incident on the well W through the transmission light quantity adjusting member 42*b* has such a light quantity distribution in which light quantity is small in a central part of the well W and becomes more toward a peripheral edge part. In this way, a light quantity on the well bottom surface can be approximated to a uniform one by increasing the incident light quantity in the peripheral edge part where the incident light is less likely to reach than in the central part. Here, it is desirable to provide a structure which facilitates an operation of matching the center of the shade pattern of the transmission light quantity adjusting member 42*b* and the center of the well W. For example, alignment marks may be previously provided for the transmission light quantity adjusting member 42*b* and the microplate M, respectively. Further, such a structure, for example, may be possible that the transmission light quantity adjusting member 42*b* is formed as a lid for covering the top of the well W while engaging with the microplate M and the alignment is automatically done by the engagement.

Figure 11:
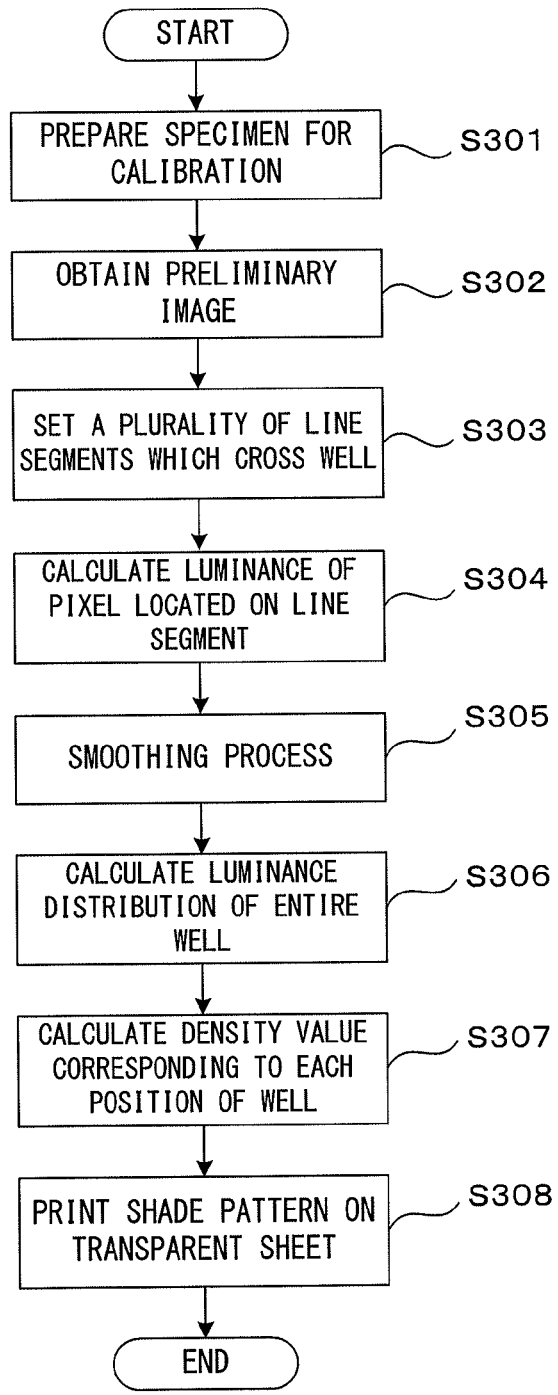
FIG. 11 is a flow chart which shows an example of a method for forming the transmission light quantity adjusting member in the fourth embodiment.

FIG. 11 is a flow chart which shows an example of a method for forming the transmission light quantity adjusting member in the fourth embodiment. First, a specimen for calibration for obtaining a light quantity distribution of illumination light in the well is prepared (Step S301). This specimen for calibration may be a specimen as an object for the imaging operation or may be separately prepared by injecting the same type and amount of fluid as the specimen into another well. Imaging is performed as in the first embodiment using the thus prepared specimen for calibration to obtain a preliminary image (Step S302).

Subsequently, a plurality of such line segments as to cross the well W are set for the thus obtained preliminary image (Step S303) and a luminance value of each pixel located on each set line segment out of a well region corresponding to the well W in the preliminary image is calculated from image data (Step S304).

Figure 12A:
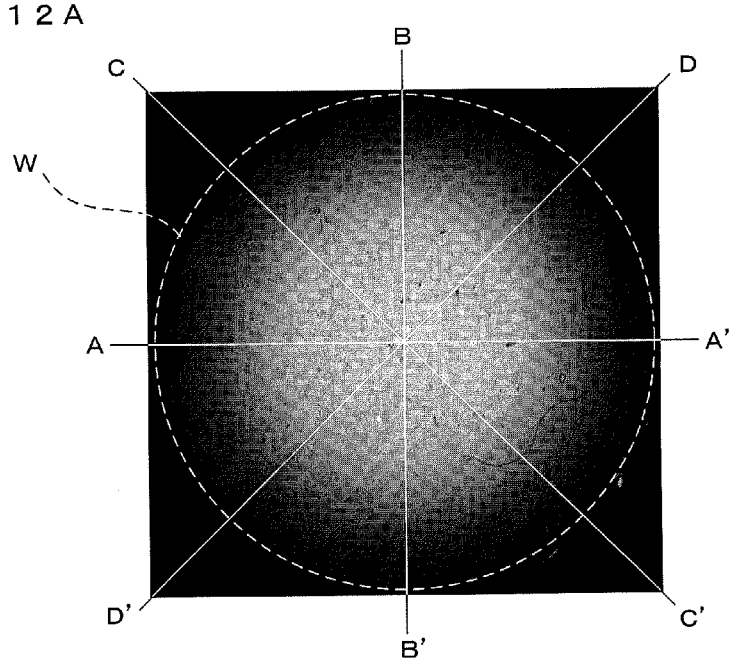
FIGS. 12A and 12B are diagrams which show an example of setting line segments.
Figure 12B:
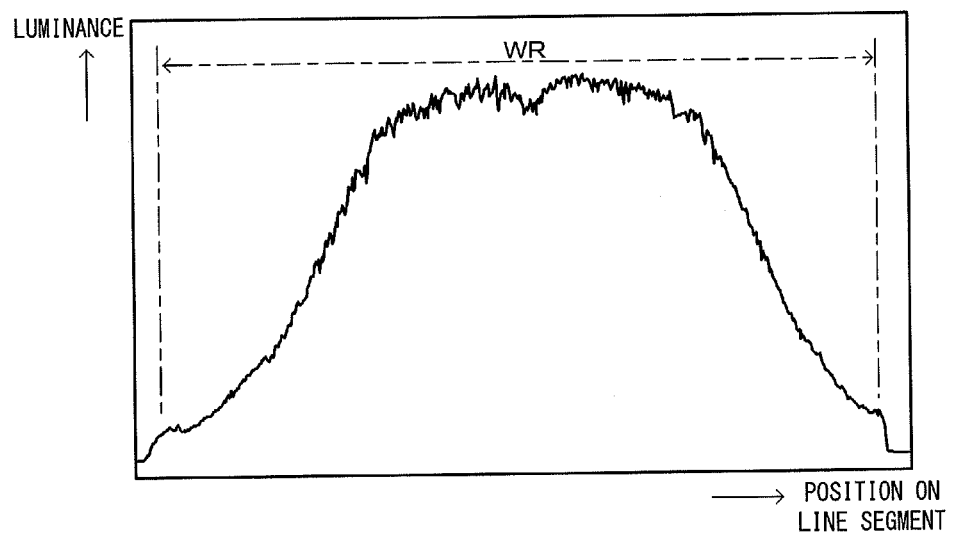

FIGS. 12A and 12B are diagrams which show an example of setting line segments. As shown in FIG. 12A, four line segments A-A', B-B', C-C' and D-D' are set for an image of one well W as an example here. The respective line segments are so set at equal angular intervals as to intersect with each other near the center of the well W. Thus, in this embodiment, an angle formed between the adjacent line segments is 45°.

FIG. 12B shows an example of a luminance profile obtained from a data string of luminance values of the respective pixels on one line segment (e.g. line segment A-A'). In conformity with the light quantity of the illumination light reaching the bottom surface of the well W which is large in a central part and small in a peripheral edge part, the luminance of each pixel is relatively high in a central part of a well region WR corresponding to the well W, whereas the luminance of each pixel is relatively low in a peripheral part of the well region WR as shown in FIG. 12B.

Although minor variations and spike noise are included in the luminance profile shown in FIG. 12B, a luminance change due to the illumination light is thought to be more moderate as described above. Accordingly, the obtained luminance profile is smoothed (Step S305). For example, a moving average processing among adjacent data or a processing of extracting an upper envelope of the waveform can be used as the smoothing.

Subsequently, a luminance distribution of the entire well W is calculated from the luminance profile obtained on each line segment (Step S306). Although a method for calculating the luminance value of each pixel in the well by an interpolation calculation from the luminance profile on each line segment is described here, it is, of course, possible to obtain the luminance distribution by a method similar to that of the first embodiment. Further, it is also possible to apply the luminance distribution calculation method of this embodiment to the first embodiment and the like.

Figure 13:
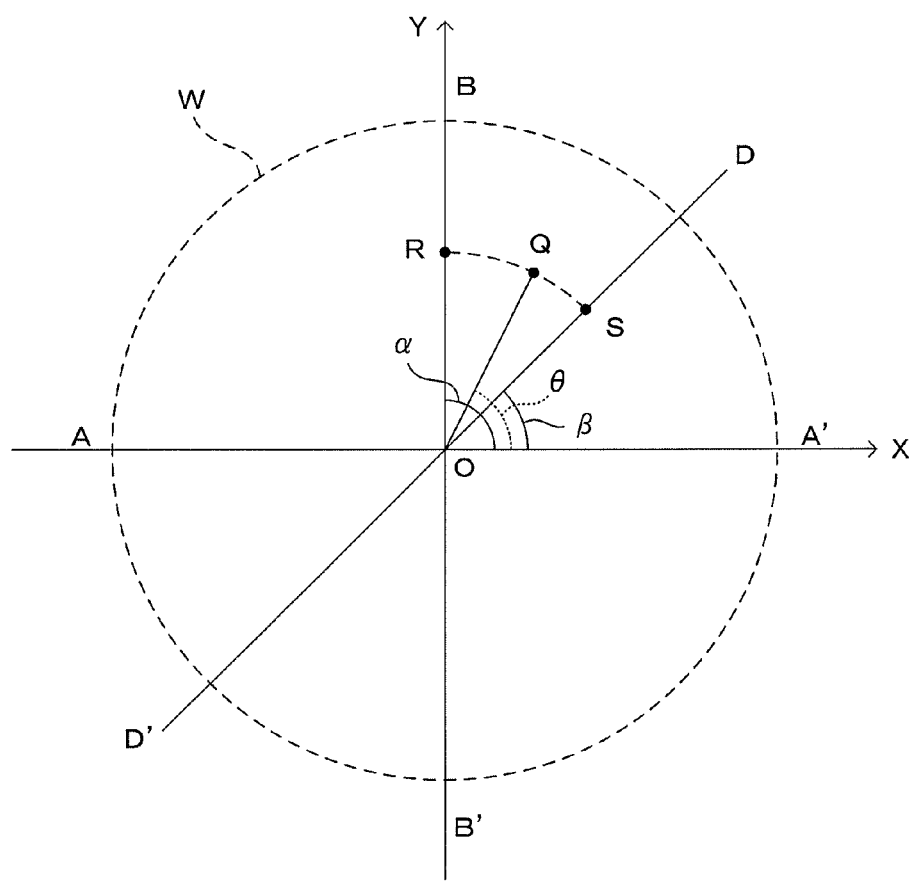
FIG. 13 is a diagram which shows a calculation principle of the luminance value of the pixel in the well.

FIG. 13 is a diagram which shows a calculation principle of the luminance value of the pixel in the well. In this method, a luminance value at one arbitrary point Q in the well W is calculated from the known luminance profile by interpolation. First, an XY plane whose origin is located on a center O of the well W is set. In an example of FIG. 13, coordinate axes are so set that the line segments A-A' and B-B' perpendicular to each other respectively coincide with an X axis and a Y axis (more precisely, these line segments are so set in advance as to coincide with the coordinate axes).

Then, two line segments at opposite sides of the point Q, the luminance value of which is to be calculated, are specified out of the line segments set in advance. In specifying these line segments, an angle of rotation of a line segment OQ connecting the origin O and the point Q and angles of rotation of the line segment A-A' and the like set in advance can be used. Specifically, when the angle of rotation of the line segment OQ centered on the origin O from one axis, e.g. the X axis is $\theta$, the line segment having the value of the angle of rotation centered on the origin O from the X axis closest to the angle $\theta$ and the line segment having the value second closest to the angle $\theta$ are specified as the line segments at the opposite sides of the point Q out of the line segments A-A', B-B', C-C' and D-D'. In the example of FIG. 13, line segments B-B', D-D' correspond to these. $\alpha$, $\beta$ respectively denote the angles of rotation of the line segments B-B', D-D' centered on the origin O from the X axis. Note that a case where the point Q is a point on any one of the line segments may be excluded. This is because the luminance value at this point Q is already obtained when the luminance profile was derived.

Subsequently, points R, S at the same distance from the origin O as the point Q on the line segments B-B', D-D' are respectively specified. The luminance values at these points R, S are already obtained and respectively denoted by Lr, Ls.

Since a light quantity change in the well W due to the illumination light source and the meniscus are moderate, the luminance value can be thought to continuously and moderately change on an arc centered on the origin O and passing through the points Q, R and S. For example, if the luminance value on this arc is assumed to be proportional to an angle of rotation of a moving radius centered on the origin O, a luminance value Lq at the point Q can be obtained as follows from a luminance value Lr at the point R on the line segment B-B', a luminance value Ls at the point S on the line segment D-D' and the values of the angles of rotation $\alpha$, $\beta$ and $\theta$ of the respective line segments.

Specifically, the following system of equations for variables m, n is solved:

$$\theta = m\alpha + n\beta$$

$$m + n = 1,$$

and the obtained values of m, n are substituted into the following equation:

$$Lq = mLr + nLs.$$

In this way, the luminance value Lq at the arbitrary point Q in the well W can be obtained. By carrying out the above calculation for each point in the well W, the luminance distribution in the entire well W can be obtained.

Referring back to FIG. 11, the method for forming the transmission light quantity adjusting member is further described. If the luminance distribution in the entire well W is calculated as described above, a density distribution of the transmission light quantity adjusting member to obtain a uniform illumination condition by canceling this luminance distribution is subsequently calculated. For the respective positions in the well W, the quantity of incident light on the well W is limited by arranging a mask pattern having a relatively high density in a region where high luminance is detected in the preliminary image and, on the other hand, more light is allowed to be incident by arranging a mask pattern having a low density in a low-density well region, thereby making it possible to uniformize the light quantity distribution of the illumination light in the well.

Specifically, a density value of the mask pattern of the pixel corresponding to each position is obtained by appropriately scaling the luminance value obtained at each position of the well W and adding an appropriate offset value if necessary (Step S307). In terms of uniformizing the light quantity distribution of the illumination light in the well W, relative density differences among the positions are more important than the absolute values of the density values. Therefore, an appropriate offset value may be added to the density value of each pixel obtained from the preliminary image for the purpose of controlling the brightness of the entire image.

Then, by forming a shade pattern having the thus obtained density corresponding to the density value at each pixel on a transparent sheet (Step S308), the transmission light quantity adjusting member 42b, for example, as shown in FIG. 10B is formed. The shade pattern can be formed, for example, by inkjet printing. Meanwhile, there may be a case that character differs in respective well W due to a combination of the well W and fluidity of the specimen and accordingly, workload for preparing the shade pattern for respective well may be excessively heavy. In such a case, it may be possible to group a plurality of wells having similar luminance distribution, obtain the shade pattern based on the luminance distribution statistically calculated in the group and commonly use the thus obtained shade pattern in the group.

Figure 14A:
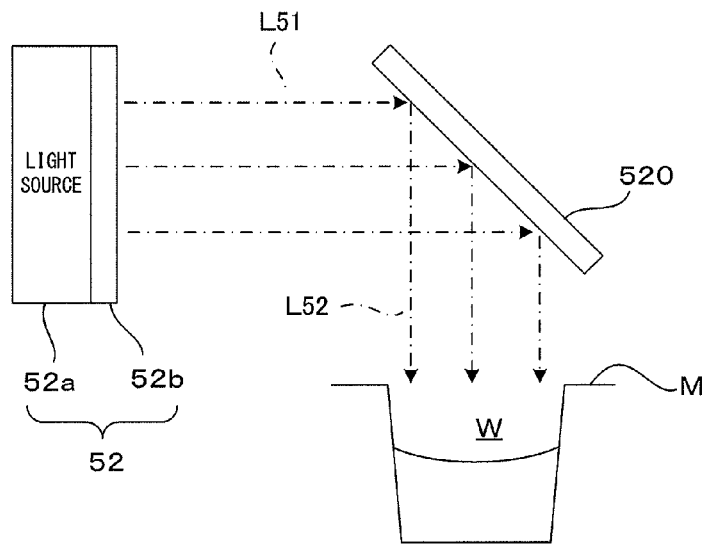
FIGS. 14A and 14B are diagrams which respectively show main parts of fifth and sixth embodiments of the imaging apparatus according to this invention.
Figure 14B:
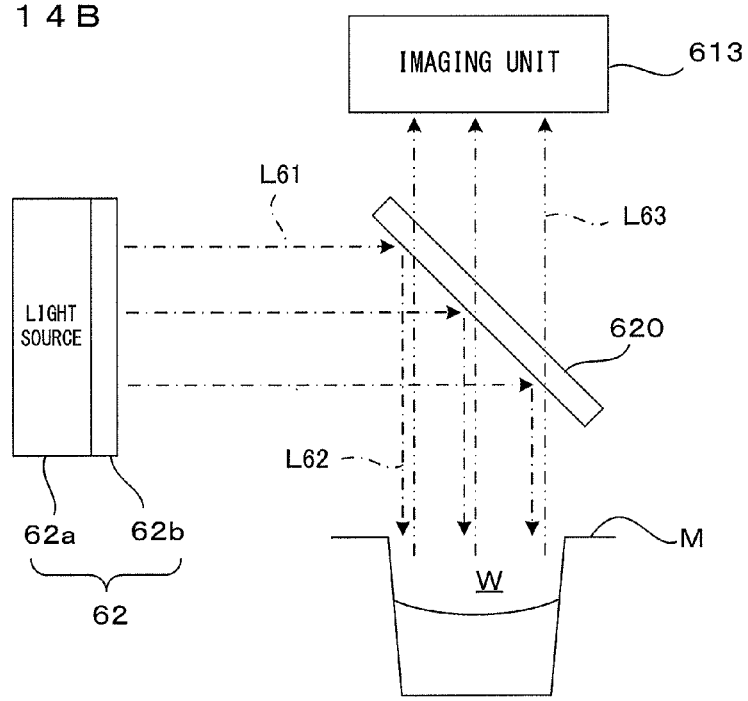

FIGS. 14A and 14B are diagrams which respectively show main parts of fifth and sixth embodiments of the imaging apparatus according to this invention. In the fifth embodiment shown in FIG. 14A, illumination light L51 from an illuminator 52 including a light source 52a and a transmission light quantity adjuster 52b is reflected by a total reflection mirror 520 and reflected light L52 is incident on a well W. Such a configuration is substantially the same as that of the first embodiment except for an optical path and effects similar to those of the first embodiment can be obtained. Further, such a structure, for example, may be possible that by using the illuminator 32 including the light source 321 and the reflecting mirror unit 322 shown in FIG. 9 instead of the illuminator 52 shown in FIG. 14A, light, whose light quantity distribution is adjusted by the illuminator 32, is reflected by the total reflection mirror 520 and incident on the specimen.

Further, in the sixth embodiment shown in FIG. 14B, an imaging unit 613 is arranged above a well W instead of arranging the imaging unit 13 below the well W as in the respective embodiments. More specifically, a half mirror 620 is provided above the well W and the imaging unit 613 is provided above the half mirror 620. Illumination light L61 emitted from an illuminator 62 including a light source 62a and a transmission light quantity adjuster 62b is caused to be incident on the half mirror 620 and reflected light L62 is caused to be incident on the well W. On the other hand, light L63 coming upward from the well W is incident on the imaging unit 613 through the half mirror 620. Even in such a case, substantially uniform light can be irradiated to an object in the well W and an image with little luminance nonuniformity can be obtained as in the above respective embodiments. Note that imaging is possible also when the illuminator 62, the half mirror 620 and the imaging unit 613 are arranged below the microplate M.

As described above, in these embodiments, the microplate M corresponds to a "specimen holding plate" of the invention and the well W corresponds to a "well" of the invention. The holder 11 functions as a "holder" of the invention, whereas the imaging unit 13 functions as an "imager" of the invention. Further, the linear imaging device 133 in the first and second embodiments corresponds to a "line sensor" of the invention. Further, the illuminators 12, 22, 32, 42, 52 and 62 function as a "light illuminator" of the invention. Further, the light emitting element 221 in the second embodiment or each group of the light emitting elements when the light emitting elements are grouped corresponds to a "light emission module" of the invention.

Further, the controllers 10 in the first to third embodiments, more specifically the shutter controller 112b in the first embodiment, the light source controller 122 in the second embodiment and the mirror controller 332 in the third embodiment function as a "controller" of the invention. Further, the transmission light quantity adjusting member 42b in the fourth embodiment functions as the "controller" of the invention.

Further, Steps S101 and S102 in the flow chart of FIG. 4 correspond to a "preliminary imaging step" of the invention, whereas Steps S103 and S104 correspond to a "detecting step" of the invention. Further, Steps S105 and S106 correspond to a "setting step" of the invention and Step S107 corresponds to an "image obtaining step" of the invention.

Note that the invention is not limited to the above embodiments and various changes other than those described above can be made without departing from the gist of the invention. For example, an arbitrary two-dimensional light quantity distribution is obtained by a combination of the surface light source and the liquid crystal shutter in the first embodiment. However, the light quantity distribution can be similarly arbitrarily set by individually controlling each light emitting element using a light source in which a multitude of light emitting elements are two-dimensionally arranged as the concept thereof is described in the second embodiment.

Conversely, an arbitrary light quantity distribution can be created by a combination of a light source having a fixed light quantity distribution and a transmission light quantity adjuster such as a liquid crystal shutter also in the second embodiment.

Further, although the liquid crystal display panel in which the surface light source and the liquid crystal shutter are united is used as the illuminator in the first embodiment, the light source and the transmission light quantity adjuster may be separately configured. Further, a diffuser or the like for uniformizing the light quantity distribution may be further provided between the light source and the transmission light quantity adjuster. An external light source may be used as the light source instead of the light source which is included in the imaging apparatus.

Although it is not particularly mentioned in the description of the above embodiments, it is sufficient to obtain a background image, on which the light quantity distribution of the illumination light is reflected, in the pre-scanning operation for obtaining a preliminary image. In this sense, a necessary resolution may be considerably lower than that in the main scanning operation. Thus, the scanning speed may be switched, such as by increasing the scanning speed of the imaging device in the pre-scanning operation to shorten a processing time and, on the other hand, by scanning the imaging device at a lower speed in the main scanning operation to obtain an image having a high resolution. Further, a more uniform illumination condition may be obtained by repeating the pre-scanning operation and the adjustment of the light quantity distribution based on the result of the pre-scanning operation a plurality of times.

Based on a similar idea, an imaging object region may be switched, such as by imaging a plurality of wells at once in the pre-scanning operation and, on the other hand, by individually imaging the wells one by one in the main scanning operation.

Further, in the case of using a color liquid crystal display panel as the transmission light quantity adjuster of the invention, the following usage is possible by changing a transmission pattern for each color. For example, an image in which the contrast of cells of a specific species is emphasized can be obtained by changing the color of the illumination light in conformity with the color of the cells as an object of analysis.

Further, the liquid crystal shutter shown as the first embodiment may be used as the transmission light quantity adjusting member in the above fourth embodiment. Further, as shown in the second embodiment, a predetermined light quantity distribution may be created by changing the emission light quantity itself from the light source.

Further, although the imaging apparatuses of the above respective embodiments are apparatuses capable of making analyses by various image processings on an imaged image, the invention can be applied also to an apparatus which merely performs only imaging.

Further, in the above respective embodiments, uniform illumination light is made incident on the object distributed in the well W by managing the light quantity distribution of light to be incident on the well W. On the other hand, in terms of preventing luminance nonuniformity in an imaged image, it is also possible to adjust the light quantity distribution on an optical path of the light coming out from the well W until this light is incident on the imaging unit as described next.

FIG. 15 is a diagram which shows an example of adjusting a light quantity distribution between a well and an imaging unit. In this example, an illuminator 72 having an appropriate in-plane light quantity distribution is provided above a microplate M including a well W and illumination light L71 is caused to be incident from above the well W. A transmission light quantity adjuster 720 similar to those used in the above respective embodiments is arranged right below the bottom surface of the well W and an imaging unit 713 is provided below the transmission light quantity adjuster 720. In such a configuration, even if light coming out from the well W has a light quantity distribution due to the nonuniformity of the illumination light, such nonuniformity is solved in light L72 to be incident on the imaging unit 713 through the transmission light quantity adjuster 720. This suppresses luminance nonuniformity in an imaged image.

By adjusting the light quantity distribution of the light to be finally incident on the imaging unit 713 in this way, the luminance nonuniformity of the image can be suppressed. Even with an imaging unit using light receiving elements whose sensitivity to light is nonlinear, it is possible to obtain an image with little influence of such nonlinearity by setting the luminance of a background part of the object at a substantially uniform level.

Note that the transmission light quantity adjuster 720 may be held in close contact with the lower surface of the microplate M. Particularly in the case of using the sheet-like member formed with the shade pattern in advance shown as the fourth embodiment as the transmission light quantity adjuster 720, such a sheet may be attached to the lower surface of the microplate M. For example, a microplate M united in advance with a sheet formed with a shade pattern can also be used.

In these inventions, the light quantity distribution of the illumination light can be, for example, so set that a larger incident light quantity is set for a position with lower luminance in a background image obtained by removing high frequency components higher than a predetermined spatial frequency from the preliminary image. The specimen as the imaging object includes cells or the like distributed in the fluid. Images of such cells or the like could cause an error in detecting nonuniformity in the light quantity of illumination light. Accordingly, the influence thereof is eliminated by removing high spatial frequency components and the light quantity can be more accurately set by detecting the luminance distribution in the remaining background image. Further, by causing more light to be incident at the position with lower luminance in the background image, it is possible to obtain an image with little luminance nonuniformity.

In the imaging apparatus according to the present invention, for example, the light illuminator may include a light source and a transmission light quantity adjuster arranged between the light source and the specimen and capable of setting a light transmission quantity for each position, and the controller may control the transmission light quantity adjuster. According to this configuration, since the light quantity distribution of the light to be finally incident on the specimen is adjusted by the transmission light quantity adjuster provided between the light source and the specimen, the light source itself is not required to have a function of finely adjusting the light quantity distribution and various light emitting devices can be used as the light source. Further, an inherent light quantity distribution of the light source itself does not affect the quality of an image.

In this case, the transmission light quantity adjuster may be capable of setting different transmission quantities for a plurality of wavelength components included in light from the light source. By doing so, a greater variety of images can be obtained by controlling a spectral distribution of light to be incident on the specimen. For example, the wavelength of the illumination light can be switched according to an imaging purpose.

A liquid crystal shutter can be, for example, used as the transmission light quantity adjuster for realizing these functions. Low-cost products capable of adjusting a transmission light quantity for each tiny pixel have already become widespread as liquid crystal shutters and the setting of a light quantity distribution according to the invention can be performed using such products.

Further, the light illuminator may include a light source in which a plurality of light emission modules are arranged and the controller individually may control light emission quantities of the light emission modules. According to this configuration, the light quantity distribution itself of the light emitted from the light source can be changed. For such an application, a light source in which a multitude of light emitting elements are arranged, for example, such as an LED (Light Emitting Diode) array can be used as the light source.

Further, for example, the light illuminator may include a light source and a plurality of reflecting mirrors configured to reflect light from the light source and cause the light to be incident on the surface of the specimen and capable of changing a reflection direction independently of each other and the controller may control the reflection direction of each of the reflecting mirrors. The light quantity distribution of the light to be incident on the specimen can be adjusted also by changing the reflection direction of the light from the light source. For such an application, a device in which a multitude of minute reflecting mirrors are arranged, for example, such as a DMD (Digital Mirror Device) can be used.

In these inventions, the image of the specimen may be obtained using a line sensor which is scanned and moved relative to the specimen holding plate. A line sensor with a high resolution preferably applicable for the use of the invention has been commercialized as a line sensor designed for imaging. By moving this to scan relative to the specimen held on the specimen holding plate, a high-quality two-dimensional image with a high resolution can be obtained.

In this case, the light illuminator may be fixedly provided with respect to the specimen holding plate or may be moved relative to the specimen holding plate integrally with the line sensor as the line sensor is moved to scan. Imaging can be performed with a sufficient light quantity by irradiating light to an imaging object region by the line sensor in either configuration. In the configuration in which the light illuminator is not moved, a surface light source capable of irradiating light to the entire surface of the recess (also including the one by a light diffuser) can be, for example, used.

Further, in the case of moving the light illuminator together with the line sensor, the set light quantity distribution can be realized by changing the light quantity distribution of the light to be incident on the surface of the specimen in synchronization with a movement of the light illuminator relative to the specimen holding plate. As a configuration for realizing such a function, a line light source (e.g. LED array) in which a multitude of light emitting elements are arranged along an arrangement direction of imaging elements in the line sensor may be used and the light emission quantity of each light emitting element may be individually controlled.

Further, in an imaging method according to this invention, the preliminary imaging step, the detecting step, the setting step and the image obtaining step are desirably performed for each specimen in the case of imaging each of specimens respectively held in a plurality of wells in a specimen holding plate. Since a surface state of the specimen and a positional relationship with a light illuminator differ from specimen to specimen, a high-quality image can be stably imaged without being affected by a variation of specimens by performing imaging with the illumination light quantity distribution individually set for each specimen.

Although this invention can be particularly preferably applied in fields requiring the observation of specimens obtained by injecting fluid into wells on a microplate used, for example, in medical and biological science fields, the fields of application thereof are not limited to the medical and biological science fields.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An imaging apparatus, comprising:
a holder that holds a specimen holding plate substantially in a horizontal state, the specimen holding plate being formed with a well capable of holding liquid;
a light illuminator that irradiates light from above the specimen holding plate held by the holder to a surface of a specimen obtained by injecting fluid into the well;
a controller that controls a light quantity distribution of light to be incident on the surface of the specimen from the light illuminator based on a luminance distribution preliminarily measured at the well with the fluid; and
an imager for obtaining an image of the specimen by imaging the specimen under light illumination at the light quantity distribution set by the controller;
wherein the controller sets the light quantity distribution of the light to be incident on the surface of the specimen based on a luminance distribution in a preliminary image obtained by imaging the well by the imager under a predetermined standard light quantity distribution; and
wherein the controller sets a larger incident light quantity for a position with lower luminance in a background image obtained by removing high frequency components higher than a predetermined spatial frequency from the preliminary image.

2. The imaging apparatus according to claim 1, wherein the light illuminator includes:
a light source; and
a transmission light quantity adjuster arranged between the light source and the specimen and capable of setting a light transmission quantity for each position, and
the controller controls the transmission light quantity adjuster.

3. The imaging apparatus according to claim 2, wherein the transmission light quantity adjuster is capable of setting different transmission quantities for a plurality of wavelength components included in light from the light source.

4. The imaging apparatus according to claim 2, wherein the transmission light quantity adjuster is a liquid crystal shutter.

5. The imaging apparatus according to claim 1, wherein:
the light illuminator includes a light source in which a plurality of light emission modules are arranged; and
the controller individually controls light emission quantities of the light emission modules.

6. The imaging apparatus according to claim 1, wherein:
the light illuminator includes a light source and a plurality of reflecting mirrors configured to reflect light from the light source and cause the light to be incident on the surface of the specimen and capable of changing a reflection direction independently of each other; and
the controller controls the reflection direction of each of the reflecting mirrors.

7. The imaging apparatus according to claim 1, wherein the imager includes a line sensor which obtains an image of the specimen by being moved relative to the specimen holding plate.

8. The imaging apparatus according to claim 7, wherein the light illuminator is moved relative to the specimen holding plate integrally with the line sensor as the line sensor is moved relative to the specimen holding plate.

9. The imaging apparatus according to claim 8, wherein the controller changes the light quantity distribution of the light to be incident on the surface of the specimen in synchronization with a movement of the light illuminator relative to the specimen holding plate.

10. An imaging method for imaging a specimen obtained by injecting fluid into a well provided in a specimen holding plate, comprising:
a preliminary imaging step of imaging the specimen and obtaining a preliminary image by irradiating light having a predetermined standard light quantity distribution toward a surface of the specimen from above the substantially horizontally held specimen holding plate;
a detecting step of detecting a luminance distribution of the preliminary image;
a setting step of setting a light quantity distribution of light to be incident on the specimen based on a detection result in the detecting step; and
an image obtaining step of obtaining an image of the specimen under light illumination at the light quantity distribution set in the setting step;
wherein a luminance distribution in a background image obtained by removing high frequency components higher than a predetermined spatial frequency from the preliminary image is obtained in the detecting step; and
a larger incident light quantity is set for a position with lower luminance in the background image in the setting step.

11. The imaging method according to claim 10, wherein the specimen is imaged by moving a line sensor relative to the specimen holding plate in the preliminary imaging step and the image obtaining step.

12. The imaging method according to claim 11, a light illuminator for irradiating light to the specimen is moved relative to the specimen holding plate integrally with the line sensor as the line sensor is moved relative to the specimen holding plate.

13. The imaging method according to claim 12, wherein imaging is performed while the light quantity distribution of the light to be incident on the surface of the specimen from the light illuminator is changed in synchronization with a movement of the light illuminator relative to the specimen holding plate based on the setting in the setting step.

14. The imaging method according to claim 10, wherein the preliminary imaging step, the detecting step, the setting step and the image obtaining step are performed for each of specimens respectively held in a plurality of wells provided in the specimen holding plate.

* * * * *